(12) United States Patent
Janatpour (10) Patent No.: US 7,448,387 B2
(45) Date of Patent: Nov. 11, 2008

(54) TRACHEOSTOMY TUBE CONNECTOR

(75) Inventor: Nina Janatpour, 2171 Hillview Dr., Walnut Creek, CA (US) 94596

(73) Assignee: Nina Janatpour, Walnut Creek, CA (US)

( * ) Notice: Subject to any disclaimer, the term of this patent is extended or adjusted under 35 U.S.C. 154(b) by 506 days.

(21) Appl. No.: 11/190,981

(22) Filed: Jul. 26, 2005

(65) Prior Publication Data

US 2007/0023050 A1    Feb. 1, 2007

(51) Int. Cl.
*A61M 11/00*    (2006.01)
(52) U.S. Cl. ................................. 128/207.14
(58) Field of Classification Search ............ 128/204.18, 128/204.19, 204.21, 207.14–207.17; 600/538–542
See application file for complete search history.

(56) References Cited

U.S. PATENT DOCUMENTS

| 4,211,240 | A | * | 7/1980 | Gallagher | 600/538 |
| 4,259,951 | A | * | 4/1981 | Chernack et al. | 128/200.14 |
| 4,579,124 | A | * | 4/1986 | Jentges | 600/538 |
| 4,852,565 | A | | 8/1989 | Eisele | |
| 6,484,724 | B1 | | 11/2002 | Sloan | |
| 6,513,519 | B2 | * | 2/2003 | Gallem | 128/200.21 |
| 6,679,250 | B2 | * | 1/2004 | Walker et al. | 128/200.21 |
| 6,904,906 | B2 | * | 6/2005 | Salter et al. | 128/200.21 |

* cited by examiner

*Primary Examiner*—Steven O Douglas
(74) *Attorney, Agent, or Firm*—Ginger R. Dreger; James A. Fox; Goodwin Procter LLP (57) ABSTRACT

Devices, systems, kits and methods are provided whereby a patient having a tracheostomy may use a respiratory therapy exercise device. A tracheostomy tube connector having features of the invention (termed a "Janatpour connector") connects a tracheostomy tube with a respiratory therapy exercise device allowing use of the respiratory therapy exercise device via a tracheostomy tube. Janatpour connectors having features of the invention include a bore allowing airflow between the tracheostomy tube and a respiratory therapy exercise device connected to each other by the Janatpour connector, and include a control port operably connected to the bore. The control port may be occluded, e.g., by a patient's finger, to provide a single airway path so that patient respiration impels airflow within the respiratory therapy exercise device. When the control port is open, air may flow out of or into the Janatpour connector via the control port as well as through the bore.

14 Claims, 4 Drawing Sheets

TRACHEOSTOMY TUBE CONNECTOR

FIELD

Devices, methods and systems useful for respiratory therapy for patients with tracheostomy tubes connected to their tracheae.

BACKGROUND

Patients in hospitals, particularly patients confined to their beds and patients recovering from surgery, trauma, or serious illness, often benefit from respiratory therapy. Common therapeutic exercises and exercise devices offered to such patients include inspiration exercises, typically with the aim of having the patient breathe deeply rather than avoid deep breathing due to fatigue, pain, or other reasons. Typically, a patient using a respiratory therapy exercise device exhales freely, and breathes in (inspires) through the respiratory therapy exercise device. A visual or other indication of the amount of the inspirational effort is typically provided, offering the patient immediate feedback regarding the amount of respiratory force produced, and providing an incentive for continued practice and improvement. For example, in one common respiratory therapy exercise device, balls are visible within transparent columns. Inspiration by the patient lifts the balls; the deeper the inspiration, the higher the ball or balls are lifted. The patient exhales freely after inspiration. Such exercises are thought to be beneficial to patients, for example, by reducing the incidence of respiratory problems such as pneumonia, and may speed recovery of the patient. Patients thought to be at risk for respiratory infections are often encouraged to use such respiratory therapy exercise devices as a way to improve lung function and reduce infections.

Such exercises and exercise devices typically require that the patient make a seal onto a tube placed into the mouth in order to provide suction through the tube to the device for the exercise. Patients having a tracheotomy (an incision in the trachea) with the resulting tracheostomy (an opening in the trachea) typically breathe via the tracheostomy, which typically has a tracheostomy tube inserted into the trachea via the tracheostomy. Tracheostomy patients are often at risk for pulmonary infections, or other respiratory problems, and quite often would benefit from such exercises. However, patients having a tracheostomy cannot provide suction through the mouth due to the tracheostomy tube placed in their trachea. Accordingly, there is need for means for providing the benefits of respiratory therapy exercises to tracheostomy patients.

SUMMARY

Connectors are provided which enable a patient having an opening in their trachea (e.g., a tracheostomy) to connect their tracheostomy tubes with respiratory therapy exercise devices and thereby gain the ability to use such devices. Such connectors may be termed "Janatpour connectors" or "JP connectors," and are termed herein "Janatpour connectors." Janatpour connectors having features of the invention are configured to engage and connect with a tracheostomy tube and configured to engage and connect with a respiratory therapy exercise device. Respiratory therapy exercise devices having features of the invention include connectors configured to engage with tracheostomy tubes. Systems, kits, and methods for connecting to, and using, respiratory therapy exercise devices are also provided, and respiratory therapy exercise devices configured to connect with a tracheostomy tube are also provided.

A Janatpour connector having features of the invention has an internal bore connecting its proximal and distal ends, and has a control port through the wall of the connector, between the proximal and distal ends. The proximal end is configured to connect with a tracheostomy tube, and the distal end is configured to connect with a respiratory therapy exercise device, or to a tube connected to a respiratory therapy exercise device. A Janatpour connector having features of the invention may connect to, and link together, a tracheostomy tube and a respiratory therapy exercise device or a tube connected to a respiratory therapy exercise device.

When open, the control port provides a shunt airway path allowing airflow into and out of the bore of the Janatpour connector through the control port, in addition to the airway path provided by the bore itself between a tracheostomy tube and a respiratory therapy exercise device connected to the Janatpour connector having features of the invention. When closed, e.g. by covering or occluding the control port (for example, by covering the control port with a portion of a finger applied to the control port) the bore remains the only path for airflow between a tracheostomy tube and a respiratory therapy exercise device.

When the control port is covered or occluded, inspiration by a patient through a tracheostomy tube connected via a Janatpour connector to a respiratory therapy exercise device will draw air through a respiratory exercise device via the bore of the Janatpour connector. A control port may serve as a vent allowing air to pass into or out of the bore of a Janatpour connector. When the control port is open, air expired by a patient through a tracheostomy tube connected via a Janatpour connector to a respiratory therapy exercise device is able to escape via the control port and need not pass through a respiratory exercise device.

In one embodiment, a Janatpour connector having features of the invention has an open proximal end and an open distal end, comprising a wall defining a bore connecting said proximal end with said distal end, said proximal end being configured to engage a tracheostomy tube, said distal end being configured to engage a respiratory therapy exercise device or a tube operably connected with a respiratory therapy exercise device, said wall further comprising a control port comprising an opening through said wall disposed between said proximal end and said distal end and operably connected with said bore.

A Janatpour connector having features of the invention may have one, or may have more than one control port through its wall. Such a control port may be configured to provide a shunt airway path connected to the bore when open, and may be configured to leave substantially only a single airway path (the bore) when the control port is closed. Such a control port may be closed by placement of at least a portion of a finger across or over the control port effective to occlude it. A control port of a Janatpour connector having features of the invention may be flush with the wall of the Janatpour connector, or may have a lip. Such a lip may extend around a portion of the perimeter of the control port, or may extend around the entire perimeter of the control port. A lip may be immediately adjacent the perimeter of the control port, or may be disposed a distance away from the perimeter of the control port. In one embodiment, the lip may extend outwardly from wall of the Janatpour connector, away from the bore, and the lip may define at least a portion of the control port opening.

A Janatpour connector having features of the invention may also have a baffle within the bore; a baffle may be effective to impede or prevent the flow of fluid or debris into a respiratory therapy exercise device, and may impede or prevent flow of fluid or debris into a tracheostomy tube. A Janatpour connector having features of the invention may have no baffles, may have one baffle, or may have more than one baffle.

A Janatpour connector having features of the invention may also have a well within the bore. A well within the bore of a Janatpour connector having features of the invention may be effective to collect fluid, and may impede or prevent fluid, secretions, condensation, or debris from going into a tracheostomy tube or into a respiratory therapy exercise device. The interior of a well is typically accessible for cleaning via the control port. In embodiments of a Janatpour connector having features of the invention, a well within a bore may have a removable portion, such as a cap, or openable bottom which may be a base of the well, effective to allow drainage or cleaning of the well. Where a well has a removable portion, such a removable portion may be pressure-fitted, or screwed on, or hinged, or otherwise removal attached. A Janatpour connector having features of the invention may have no wells, may have one well, or may have more than one well.

In some embodiments, a Janatpour connector having features of the invention may have a baffle and not have a well. In some embodiments, a Janatpour connector having features of the invention may have a well and not have a baffle. In some embodiments, a Janatpour connector having features of the invention may have a baffle and have a well within the bore. In some embodiments, a well may be disposed within a bore effective to collect fluid, condensation, secretions or debris directed to it by the baffle. In some embodiments, a well may be disposed so as to collect fluid, condensation, secretions or debris contacting or accumulating on a baffle. In some embodiments, a well may be disposed substantially opposite a baffle.

An embodiment of devices having features of the invention includes a respiratory therapy exercise device configured to include a Janatpour connector as an integral part of the respiratory therapy exercise device. In embodiments of devices having features of the invention, a respiratory therapy exercise device may have a bore within a tube, the tube being configured to connect with a tracheostomy tube and having one or more control ports. Such a control port may be configured to provide a shunt airway path connected to the bore when open, and may be configured to leave substantially only a single airway path (the bore) when the control port is closed. Such a control port may be closed by placement of at least a portion of a finger across or over the control port effective to occlude it. A respiratory therapy exercise device having features of the invention may have no baffle, or no well, or may include a baffle, more than one baffle, a well, more than one well, a baffle and a well, a baffle with more than one well, a well with more than one baffle, or more than one baffle and more than one well, within the bore of the device.

Also provided are systems including a respiratory therapy exercise device and a Janatpour connector that are operably connected and configured effective to provide an airflow pathway between the Janatpour connector and the respiratory therapy exercise device. Kits including a Janatpour connector, a respiratory therapy exercise device and/or instructions for their use are also provided.

Respiratory therapy exercise methods for patients in need of respiratory exercise with a respiratory therapy exercise device are also provided. In one embodiment, a respiratory therapy exercise method for such a patient having a trachea, a tracheostomy and a tracheostomy tube connected to the trachea includes (a) connecting a Janatpour connector having a control port to a tracheostomy tube connected to the patient's trachea; (b) connecting the Janatpour connector to a respiratory therapy exercise device, effective to operably connect said tracheostomy tube and said trachea to a respiratory therapy exercise device; and (c) occluding the control port effective to provide the patient with respiratory therapy exercise upon inspiration by the patient. In one embodiment of the methods, the control port may be occluded by a portion of a finger, such as by a portion of the patient's finger. In an embodiment, a lid may be disposed near a control port, which lid is typically sized and shaped so as to be able to completely cover a control port, and may at least partially cover or at least partially occlude the control port. A lid for at least partially occluding or covering a control port may be operable by a finger, or by other means. In embodiments, a lid may be provided effective to completely cover the control port effective to completely occlude it when desired.

Janatpour connectors, systems, kits, methods, and respiratory therapy exercise devices provided herein enable a patient having a tracheostomy to use respiratory therapy exercise devices. Such patients have been unable to readily use respiratory therapy exercise devices in the past. This inability to take advantage of such exercises and devices has prevented these patients from obtaining the benefits of improved respiration, speedier recovery from surgery or illness, and reduced risk of infection and complications following illness or medical procedures offered by such exercises and devices. The Janatpour connectors, systems, kits, methods, and respiratory therapy exercise devices provided herein provide tracheostomy patients with the ability to use respiratory therapy exercise devices and to improve their respiration and reduce infection and complications following medical and/or surgical procedures.

DETAILED DESCRIPTION

Figure 1:
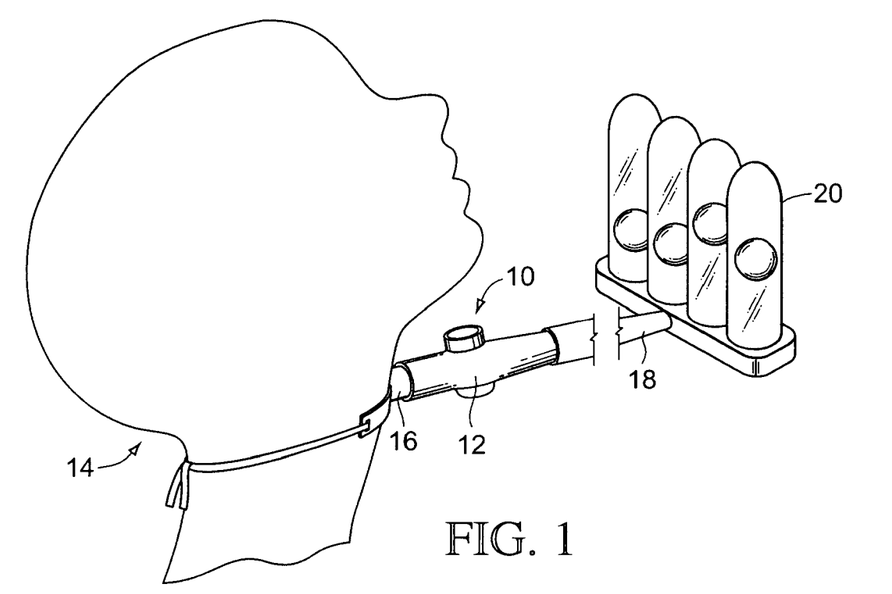
FIG. 1 provides a schematic view of a system including a connector having features of the invention. A patient having a tracheostomy is shown, the tracheostomy tube being connected to a Janatpour connector having features of the invention which is connected to a respiratory therapy exercise device, allowing the patient to perform respiratory therapy exercises.

As illustrated in FIG. 1, a system 10 having features of the invention may include a Janatpour connector 12 having features of the invention. A patient 14 having a tracheostomy is shown, with a tracheostomy tube 16 emerging from the tracheostomy. The tracheostomy tube 16 being connected to a Janatpour connector 12 having features of the invention which is connected to a tube 18 connected to (or part of) respiratory therapy exercise device 20, allowing the patient 14 to perform respiratory therapy exercises.

A Janatpour connector 12 having features of the invention is illustrated in FIG. 2. FIG. 2A is a schematic view, and FIG. 2B is a top view of a Janatpour connector 12 having features of the invention. FIGS. 2C, 2D, 2E, and 2F show further views of the Janatpour connector 12 of FIG. 2A. A longitudinal cross-sectional view (2C, taken along line C-C of FIG. 2B), and transverse cross-sectional views (2D, taken along line D-D of FIG. 2C, FIG. 2E taken along the line E-E of FIG. 2C), and FIG. 2F, taken along the line F-F of FIG. 2C) are shown in FIG. 2.

The Janatpour connector 12 has a proximal end 22, a distal end 24, and a control port 26. The outer surface 28 of the Janatpour connector 12 shown in FIG. 2 has a bulge 30. The inner surface 32 defines an axial bore 34 through the Janatpour connector 12. The inner surface 32 of the Janatpour connector 12 defines a well 36 within the bore 34; bulge 30 providing an indication of the shape of the well 36 within bore 34. Control port 26 has a lip 38 having an outer surface 40 and an inner surface 42. Inner surface 42 defines the control port bore 44 of control port 26 which is continuous with bore 34 through the Janatpour connector 12. A lip 38 may extend a suitable distance from the outer surface 40. For example, a lip 38 may extend about 1 mm to about 10 mm, or about 1 mm to about 5 mm from the outer surface 28.

Figure 2A:
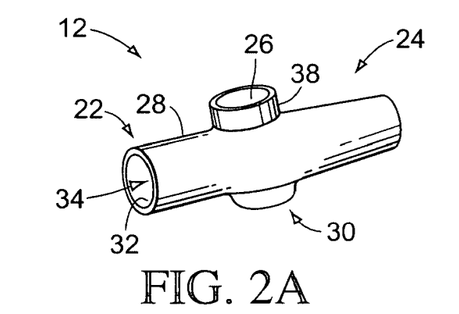
FIG. 2A provides a schematic view of a Janatpour connector having features of the invention having a control-port with a lip.
Figure 2B:
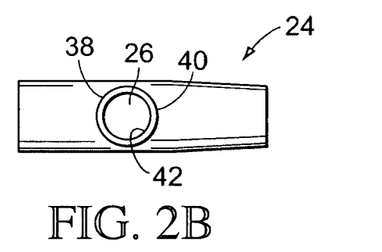
FIG. 2B provides a top view of the Janatpour connector having features of the invention of FIG. 2A.
Figure 2C:
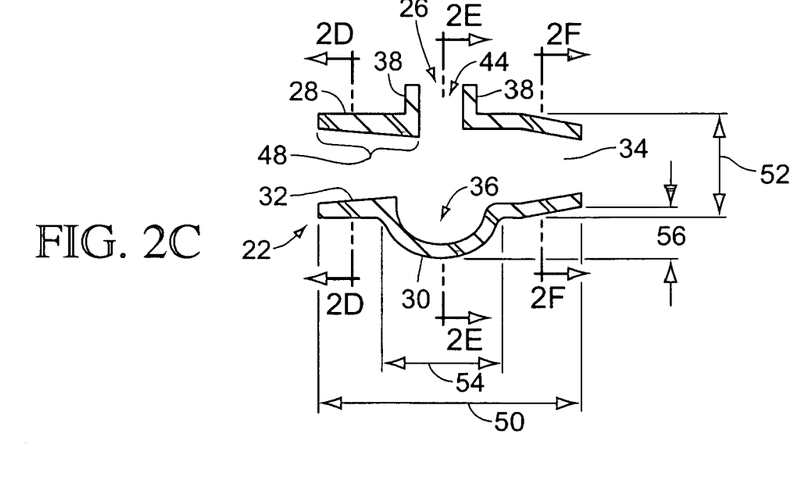
FIG. 2C provides a longitudinal cross-sectional view of the Janatpour connector having features of the invention of FIG. 2A.
Figure 2D:
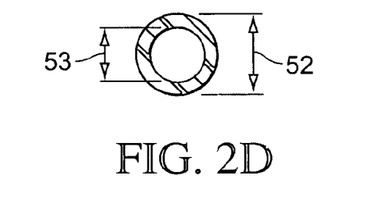
FIG. 2D provides a transverse cross-sectional view of the Janatpour connector having features of the invention of FIG. 2A along the line D-D of FIG. 2C.

Outer surface 28 is tapered at its distal portion 24, having a tapered portion 46 effective to connect with a tube 18 connected to (or part of) a respiratory therapy exercise device 20. Such a connection is effective to engage and to provide a substantially air-tight connection between a tube 18 and a Janatpour connector 12. Inner surface 32 is tapered at its proximal portion 22, having a tapered portion 48 effective to connect with a tube 16. Such a connection between a Janatpour connector 12 and a tube 18 and/or a tube 16 is effective to engage and to provide a substantially air-tight connection between a tube 18 and/or a tube 16 and a Janatpour connector 12. Tapered portions 46 and 48 may be of any length suitable for engaging a tube or tube fitting. For example, tapered portions 46 and 48 may have lengths of about 5 mm to about 30 mm, or about 10 mm to about 20 mm, or about 15 mm.

Figure 2E:
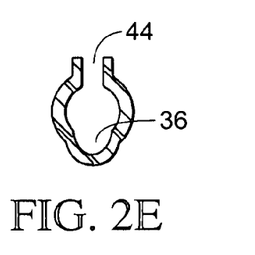
FIG. 2E provides a transverse cross-sectional view of the Janatpour connector having features of the invention of FIG. 2A along the line E-E of FIG. 2C.
Figure 2F:
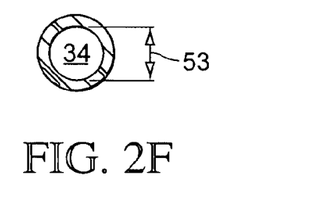
FIG. 2F provides a transverse cross-sectional view of the Janatpour connector having features of the invention of FIG. 2A along the line F-F of FIG. 2C.

As indicated in FIG. 2C and 2E a well 36 may be defined by a depression in inner surface 32. A well 36 may have a well width 54 of about 20 mm, or about 30 mm, or about 40 mm, or about 50 mm, or about 60 mm, or about 70 mm, or about 80 mm, or about 90 mm. A well 36 may have a well depth 56 of about 5 mm, or about 10 mm, or about 15 mm, or about 20 mm, or about 30 mm, or about 40 mm, or about 50 mm.

Thus, axial bore 34 and control port bore 44 provide pathways for airflow within Janatpour connector 12. Such airflow may be, for example, through, into, or out of Janatpour connector 12.

A Janatpour connector 12 having features of the invention may be of any suitable size. For example, a Janatpour connector 12 may have a length 50 of about 10 to about 100 mm, or about 20 to about 80 mm, or about 30 to about 70, or about 40 to about 60, or about 45 to about 50 mm. A Janatpour connector 12 may have a diameter 52 of about 5 to about 50 mm, or about 11 to about 30 mm, or about 15 to about 25 mm, or about 18 mm to about 22 mm. A Janatpour connector 12 may have an inner diameter 53 of about 2 to about 40 mm, or about 5 to about 30 mm, or about 10 to about 25 mm, or about 12 mm to about 22 mm, or about 14 to about 18 mm. It will be understood that the outer diameter 52 and the inner diameter 53 may optionally vary along the length 50 of a Janatpour connector 12, or optionally along a portion or portions of the length 50 of a Janatpour connector 12.

Well 36 is configured effective to collect fluid, such as vapor, sputum, condensation, secretions, or other fluid, or debris, allowing axial bore 34 to remain clear and open for airflow leading into and out of a tracheostomy tube 16 connected to a connector 12. Well 36 may be cleaned (e.g., fluid removed) via control port 26 by a swab, aspirator, or other means.

As indicated in FIG. 3, a Janatpour connector 58 having features of the invention may include a baffle 60. The schematic view shown in FIG. 3A depicts a baffle 60, the cut-away portion making visible an internal baffle 60 positioned above a sputum well 62. FIG. 3B provides a longitudinal cross-sectional view (taken along the line B-B), and FIG. 3C provides a transverse cross-sectional view (taken along line C-C), of a Janatpour connector 58 having a baffle 60. A baffle 60 may be disposed within the internal bore 62 of a Janatpour connector 58 at an angle 64 which may be between about 10° and about 80°, or between about 20° and about 70°, or between about 30° and about 60°, or between about 40° and about 50°.

Figure 3A:
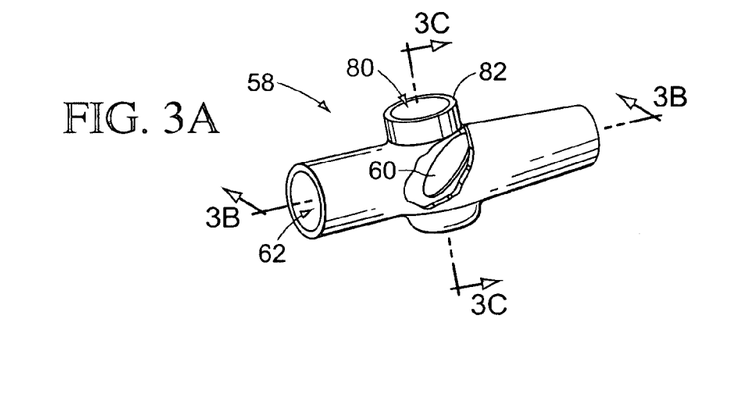
FIG. 3A provides a schematic view with cut-away section of a Janatpour connector having features of the invention, the cut-away portion making visible an internal baffle positioned near a sputum well.
Figure 3B:
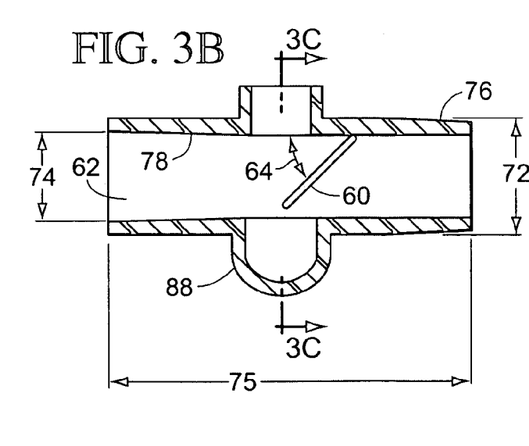
FIG. 3B provides a longitudinal cross-sectional view of the Janatpour connector of FIG. 3A taken along the line B-B.
Figure 3C:
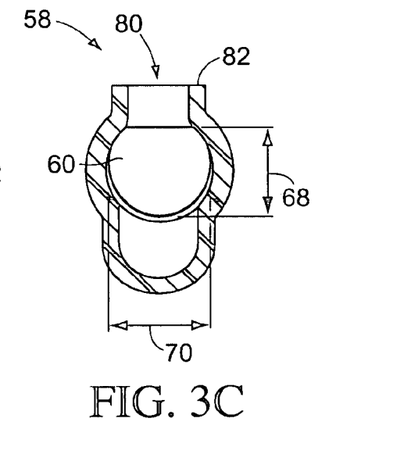
FIG. 3C provides a transverse cross-sectional view of the Janatpour connector of FIG. 3A taken along line C-C of FIGS. 3A and 3B.

A baffle 60 is configured to deflect or prevent sputum, condensation, secretions, or other fluid, or debris, from being aspirated into a tracheostomy tube connected to a tracheostomy connector 58 or to flow into a respiratory therapy exercise device 20. A baffle 60 may also be configured to aid in collecting fluid, including sputum, condensation, secretions, or other fluid, or debris, in a well 66. A well 66 and a baffle 60 may be disposed relative to each other so that fluid will be collected in a well 66. In some embodiments, a well 66 is substantially opposite a baffle 60 effective to collect fluid or debris collected or deflected by a baffle 60. In some embodiments, a well 66 is offset and substantially opposite a baffle 60 to better collect fluid draining off a baffle 60, e.g., where a baffle 60 has a surface that is angled so that fluid or debris draining or deflected from the baffle 60 will flow or fall into a well 66 positioned at a location that is offset and not directly opposite the baffle 60. For example, a well 66 may be offset from directly opposite a baffle 60 at a position such that a line extended along the angle of the baffle surface passes through the well 66. A baffle 60 may be of a size and may have dimensions effective to partially occlude an internal bore 62. For example, a baffle 60 may have a baffle length 68 approximately equal to the diameter of an internal bore 62, so that being disposed at an angle 64 not equal to 90° the baffle 60 occludes some but not all of the internal bore 62. For some angles 64 a baffle 60 may have a baffle length 68 that may be somewhat greater than the diameter of an internal bore 62, effective that the baffle 60 occludes some but not all of the internal bore 62. A baffle 60 may alternatively have a baffle length 68 less than the diameter of an internal bore 62, so that if it were disposed at any angle 64 the baffle 60 would only partially occlude the internal bore 62. In some embodiments, a baffle 60 may have a baffle length 68 of about 5 mm, or about 10 mm, or about 15 mm, or about 20 mm, or about 25 mm, or about 30 mm, or about 40 mm, or about 50 mm. A baffle width 70 may also be configured to partially occlude an internal bore 62, and may have a baffle width 70 of about 5 mm, or about 10 mm, or about 15 mm, or about 20 mm, or about 25 mm, or about 30 mm, or about 40 mm, or about 50 mm.

In some embodiments, a Janatpour connector 58 having features of the invention may have an outer diameter 72 of about 10 mm to about 30 mm, or about 15 mm to about 25 mm, or about 20 mm. In some embodiments, a Janatpour connector 58 having features of the invention may have an inner diameter 74 of about 10 mm to about 30 mm, or about 15 mm to about 25 mm, or about 20 mm. In some embodiments, a Janatpour connector 58 having features of the invention may have an outer diameter 72 of about 20 mm and an inner diameter 74 of about 16 mm. A Janatpour connector 58 having features of the invention may have a length 75 of about 5 mm to about 300 mm, or about 7 mm to about 200 mm, or about 10 mm to about 100 mm, or about 20 to about 90 mm, or about 50 to about 80, or about 55 to about 75 mm, or about 65 mm. The proximal end and the distal end of a Janatpour connector having features of the invention may independently be tapered, or may independently have no taper.

A Janatpour connector having features of the invention is configured to engage other elements, e.g., to engage a respiratory therapy exercise device and to engage a tracheostomy tube. In some embodiments, the outer surface of the proximal end of a Janatpour connector is tapered to be received within a bore of a tracheostomy tube. In some embodiments, the inner surface of the proximal end of a Janatpour connector is tapered to receive a tracheostomy tube within the bore of the Janatpour connector. In further embodiments, the proximal end of a Janatpour connector having features of the invention has no taper. In each of these examples, the proximal end of a Janatpour connector having features of the invention is configured to engage a tracheostomy tube, and to provide an engagement effective to provide a substantially air-tight connection between a tracheostomy tube and the proximal end of a Janatpour connector.

In some embodiments, the outer surface of the distal end of a Janatpour connector is tapered to be received within a bore of a portion of a respiratory therapy exercise device or of a tube connected to a respiratory therapy exercise device. In some embodiments, the inner surface of the distal end of a Janatpour connector is tapered to received a portion of a respiratory therapy exercise device or of a tube connected to a respiratory therapy exercise device within the bore of the Janatpour connector. In further embodiments, the distal end of a Janatpour connector having features of the invention has no taper. In each of these examples, the distal end of a Janatpour connector having features of the invention is configured to engage a portion of a respiratory therapy exercise device or of a tube connected to a respiratory therapy exercise device, and to provide an engagement effective to provide a substantially air-tight connection between the portion of a respiratory therapy exercise device or tube connected to a respiratory therapy exercise device and the distal end of a Janatpour connector.

Thus, in some embodiments, an outer diameter 72 of a Janatpour connector 58 having features of the invention may have different values along the length 75 of the Janatpour connector 58, so as to have a tapered outer surface distal portion 76 as indicated in the Figures. In some embodiments, an outer surface distal portion 76 is not tapered. In other embodiments, an inner surface proximal portion 78 of a Janatpour connector 58 having features of the invention is not tapered. In other embodiments, an inner diameter 74 may have different values along the length of the Janatpour connector 58, having a tapered inner surface proximal portion 78 as indicated in the figures. Such tapered portions may be inner surfaces or outer surfaces, as well as proximal or distal portions, and may be configured to engage non-tapered tubes, complementary tapered portions of tubes, connectors, or other elements, such as fittings (e.g., Luer or other standard fittings, or non-standard fittings). Such an engagement is effective to provide a substantially air-tight connection between a Janatpour connector 58 having features of the invention and a tracheostomy tube, or other tube, or fitting, such as a tube or fitting of a respiratory therapy exercise device. Tapered portions 76 and 78 may be of any length suitable for engaging a tube or fitting. For example, tapered portions 76 and 78 may have lengths of about 5 mm to about 30 mm, or about 10 mm to about 20 mm, or about 15 mm.

In some embodiments of a Janatpour connector 58 having features of the invention, an outer diameter 72 may be about 23 mm in some portions, and may be about 19 mm in a tapered portion. In embodiments, an outer diameter 72 may be about 22 mm in some portions, and may be about 20 mm in a tapered portion. In embodiments, a tapered portion may taper over a length of about 5-30 mm, or over a length of about 10-20 mm or over a length of about 15 mm. In embodiments of a Janatpour connector 58 having features of the invention, an inner diameter 74 may be about 17 mm in some portions, and may be about 13 mm in a tapered portion. In embodiments, an inner diameter 74 may be about 16 mm in some portions, and may be about 14 mm in a tapered portion.

Figure 3D:
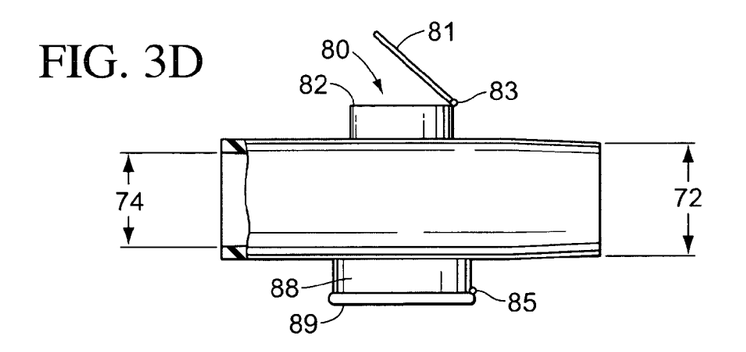
FIG. 3D is a schematic illustration of an embodiment of a Janatpour connector having a cap or lid configured to cover the control port and having a cap allowing access to the well.

A Janatpour connector 58 having features of the invention may have a control port 80. As indicated in the figures, a control port 80 may have a lip 82. In embodiments of a Janatpour connector 58 having features of the invention, a control port 80 may lack a lip 82, and be flush, or substantially flush, with the outer surface 84 of the Janatpour connector 58. A lip 82 may be of any suitable size, and typically encompasses the entire perimeter of a control port 80, although a lip 82 need not extend completely around the perimeter of a control port 80, and need not be continuous. A control port 80 may have a control port inner diameter 86 of about 2 to about 20 mm, or about 5 to about 10 mm. In embodiments of a Janatpour connector 58, a control port inner diameter 86 may be about 3 mm, or about 5 mm, or about 7 mm, or about 10 mm, or about 12 mm. In embodiments of a Janatpour connector 58 having features of the invention, a control port 80 may be configured to receive a portion of a human finger, and to be occluded or closed by application of a portion of a human finger. As illustrated in FIG. 3D, in some embodiments of a Janatpour connector 58 having features of the invention, a control port 80 may optionally have a lid or cap 81 which may cover the control port. A lid or cap 81 may optionally have a hinge 83.

A Janatpour connector 58 having features of the invention may have a well 88 configured effective to collect fluid, such as vapor, sputum, or other fluid, or debris, allowing internal bore 62 to remain clear and open for airflow leading into and out of a tracheostomy tube 16 connected to a Janatpour connector 58. Well 88 may be cleaned (e.g., fluid removed) via control port 80 by a swab, aspirator, or other means. In embodiments of a Janatpour connector 58 having features of the invention, a well 88 may have a rounded bottom in order to facilitate cleaning. A well 88 may have any suitable shape. A well 88 may be configured to open for cleaning or drainage, and may have a cap portion 89 that screws onto or snaps onto another portion of a well 88 (see, e.g., FIG. 3D). A lid or cap 89 may optionally have a hinge 85.

Figure 4A:
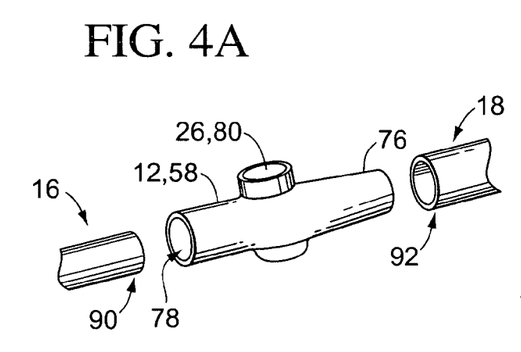
FIG. 4A provides a schematic illustration of portions of a system as illustrated in FIG. 1, the portions of the system being shown in a disassembled configuration, including a Janatpour connector having features of the invention, a portion of a tracheostomy tube, and a portion of a tube connected to a respiratory therapy exercise device.
Figure 4B:
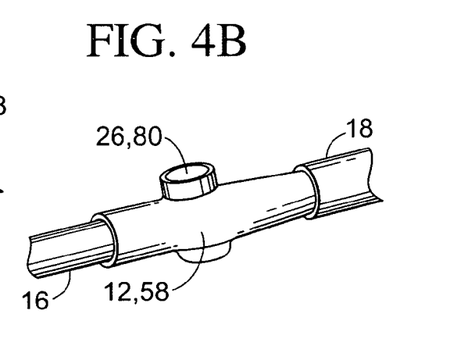
FIG. 4B provides a schematic illustration of portions of a system as illustrated in FIG. 2, the portions of the system being shown in an assembled configuration, including a Janatpour connector having features of the invention, a portion of a tracheostomy tube, and a portion of a tube connected to a respiratory therapy exercise device.

As illustrated schematically in FIG. 4, a Janatpour connector 12 or 58 having features of the invention may be readily connected to a tracheostomy tube 16 and to a tube 18 connecting to (or part of) a respiratory therapy exercise device 18. FIG. 4A shows a Janatpour connector 12 or 58 having features of the invention close to, but not connected to, a portion of a tracheostomy tube, and a portion of a tube connected to (or part of) a respiratory therapy exercise device. FIG. 4B shows the elements depicted in FIG. 4A assembled together effective to connect Janatpour connector 12 or 58 with a tracheostomy tube 16 and a respiratory therapy exercise device 18.

As illustrated in FIG. 4, a distal portion 90 of the tracheostomy tube 16 fits snugly into the tapered inner surface proximal portion 78 to form a stable and substantially air-tight connection. A distal portion 92 of the tube 18 connected to (or part of) a respiratory therapy exercise device 20 fits snugly to the outer surface distal portion 76 to form a stable and substantially air-tight connection. When assembled together, a continuous airway path is provided between a tracheostomy tube 16 and a respiratory therapy exercise device 20 via a Janatpour connector 12 or 58 having features of the invention. Occlusion of a control port 26 or 80 is effective to prevent airflow into or out of a control port 26 or 80, so that airflow into or out of a tracheostomy tube 16 in such a situation is constrained to be through an internal bore 32 or 62. It will be understood that a Janatpour connector having features of the invention may connect with a tracheostomy tube in any suitable manner, and may connect with a respirator therapy exercise device in any suitable manner. For example, a portion of an element illustrated as fitting inside another portion of another element may, in embodiments, fit around the other portion instead, or portions of elements may connect to each other without one portion fitting inside another.

Figure 5A:
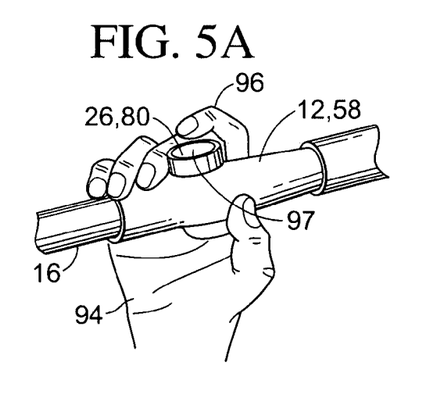
FIG. 5A provides a schematic illustration of a portion of a system as illustrated in FIG. 1, the system being shown in an assembled configuration, further showing the hand of a patient with a finger over the control port but not occluding the control port, providing a shunt airway path and an airway connection to a respiratory therapy exercise device. With the control port open, a patient may exhale and/or breathe via the control port while connected to the Janatpour connector, and may relax and breathe normally between exercise sessions or during breaks during an exercise session.
Figure 5B:
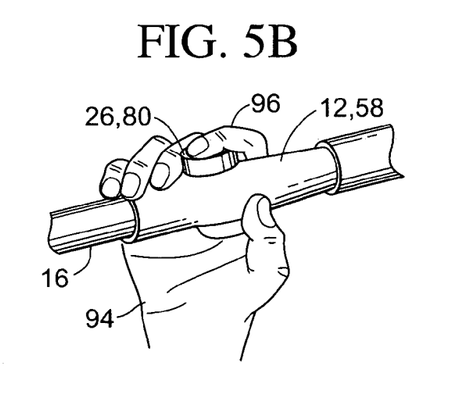
FIG. 5B provides a schematic illustration of a portion of a system as illustrated in FIG. 1, the system being shown in an assembled configuration, further showing the hand of a patient with a finger occluding the control port so as to block the shunt airway path, allowing the patient to use the respiratory therapy exercise device connected to the Janatpour connector. Typically, such use includes the patient inspiring while occluding the control port, so that inspirational airflow is substantially via the respiratory therapy exercise device and the tube connecting it to the Janatpour connector. While the control port is open, airflow (e.g., exhalation) is not directed to, from or through the respiratory therapy exercise device.

Use of a Janatpour connector having features of the invention is illustrated in FIGS. 5A and 5B. A Janatpour connector having features of the invention may be used while connected to a tracheostomy tube 16 and to a respiratory therapy exercise device. A hand 94 of a patient 14 is shown holding onto the Janatpour connector 12 or 58, with a finger 96 shown raised and near to a control port 26 or 80. Placing a finger onto the aperture 97 occludes the control port 26 or 80, so that airflow into or out of a tracheostomy tube 16 in such a situation is constrained to be through an internal bore 32 or 62, as illustrated in FIG. 5B. Typical uses of such a device and assembly include inspiration (breathing in) of the patient, via a connected respiratory therapy exercise device in order to exercise the respiratory system, to provide improved ventilation, and to reduce the risk of respiratory tract infections. For example, when a patient 14 inspires while occluding the control ports 26 and 80, airflow is substantially constrained to be via the respiratory therapy exercise device 20 and the tube connecting it to the Janatpour connector 12.

Alternative methods, systems and apparatus to the inventions are discussed in FIG. 6. A schematic illustration of an alternative embodiment having features of the invention is shown in FIG. 6A, including a respiratory therapy exercise device 98 configured to connect to a tracheostomy tube 16, having a control port 100 on a terminal portion 102 of a tube 104 connected to the body of the respiratory therapy exercise device. In the system illustrated in FIG. 6A, the connector 106 forms a portion of the tube 104, so that connections are with a tracheostomy tube 16 may be temporary while the connection corresponding to that of a respiratory therapy exercise device 98 may be more permanent.

Figure 6A:
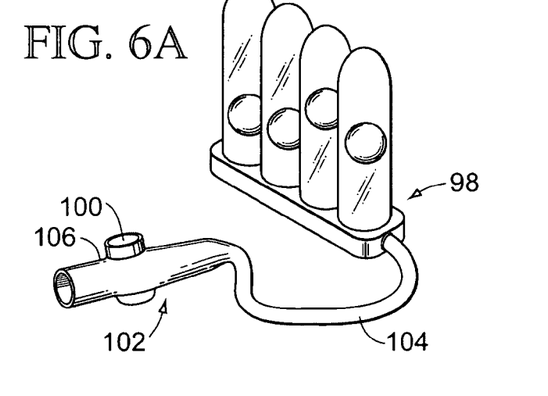
FIG. 6A provides a schematic illustration of an alternative embodiment having features of the invention, including a respiratory therapy exercise device configured to connect to a tracheostomy tube, having a control port on a terminal portion of a tube connected to the body of the respiratory therapy exercise device.
Figure 6B:
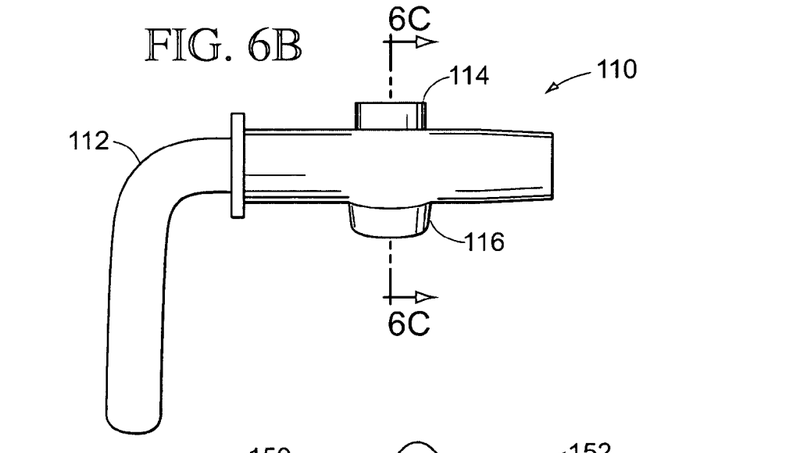
FIG. 6B provides a schematic illustration of an alternative embodiment having features of the invention, providing an alternative tracheostomy tube device including a tracheostomy tube having a control port on a terminal portion of the tracheostomy tube and being tapered to fit into a respiratory therapy exercise device or a tube connected to a respiratory therapy exercise device.
Figure 6C:
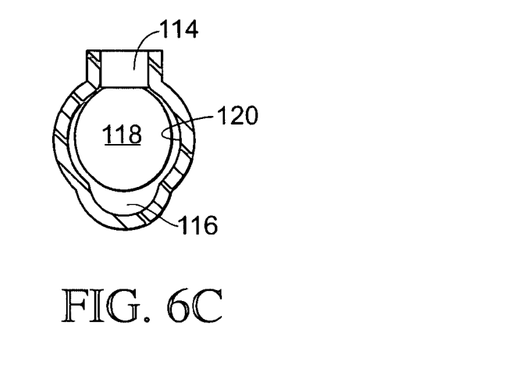
FIG. 6C provides a cross-sectional illustration of the alternative embodiment having features of the invention of FIG. 6B, showing a baffle within the internal bore of the terminal portion of the alternative tracheostomy tube device.

FIGS. 6B and 6C show an alternative embodiment having features of the invention, providing an alternative tracheostomy tube device 110 including a tracheostomy tube portion 112 having a control port 114 and a well 116 on a terminal portion of the tracheostomy tube device 110. In embodiments of a tracheostomy tube device 110 as exemplified in FIGS. 6B and 6C, a tracheostomy tube device 110 including the combined functionality of a tracheostomy tube and a Janatpour connector is provided. A patient with a stoma may insert a device 110 into the stoma and trachea providing a single device for connecting to a respiratory therapy exercise device. A well 116 may be optional, so that in some embodiments of an alternative tracheostomy tube device 110, a well 116 is absent. As indicated in FIG. 6C, an alternative tracheostomy tube device 110 may optionally also include a baffle 118 within the internal bore 120 of the terminal portion of the alternative tracheostomy tube device 110.

Figure 6D:
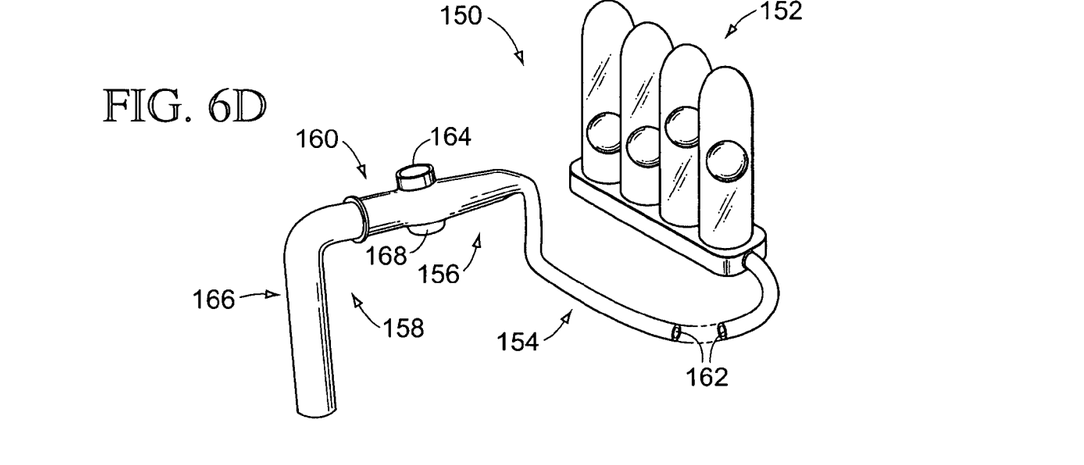
FIG. 6D provides a schematic illustration of an alternative embodiment having features of the invention: a device combining a respiratory therapy exercise device, a tracheostomy tube and a Janatpour connector.

FIG. 6D illustrates a further embodiment of devices having features of the invention, showing a device 150 combining features of a tracheostomy tube, a Janatpour connector, and a respiratory therapy exercise device. A device 150 having features as illustrated in FIG. 6D includes respiratory therapy exercise device portion 152 connected via a connecting portion 154 to a Janatpour connector portion 156 connected to a tracheostomy tube portion 158, such that a tracheostomy tube is at a terminal portion 160 of the device 150, and a connecting portion 154 comprising a tube or conduit having a bore 162 with a control port 164 having features of the invention connects to a respiratory therapy exercise device portion 152, providing a respiratory therapy exercise device, a Janatpour connector and a tracheostomy tube all as one unit. The connecting portion 154 is shown as a continuous tube in FIG. 6D (a cut-away portion, indicated by the dotted lines, is shown to illustrate the internal bore 162 of the connecting portion 154) although it will be understood that a connecting portion 154 having a bore 162 need not be tubular and may have any external or internal shape. A device 150 may include a well 168. The tracheostomy tube portion 158 of a device 150 as illustrated in FIG. 6D has a terminal portion 166 that is configured to fit within a trachea of a patient having a stoma (the stoma being capable of accepting a tracheostomy tube for insertion), or within the trachea of a patient having any other means for accessing their trachea.

Janatpour connectors 12 and 58 and devices 98 and 110 having features of the invention may be made of any suitable material, which is preferably sterilizable, durable, sturdy, and inexpensive. Such a suitable material may be, for example, a bio-compatible material, such as a bio-compatible polymer, ceramic, composite, or metal. Thus, for example, such connectors may be made from plastic, thermoplastic elastomers, glass, metal, carbon fibers, natural and synthetic rubbers, polymeric materials, including, for example, polyether block amides, NYLON®, HYTREL®, high density polyethylene (HDPE), polyvinyl chloride, poly(esters), poly(amides), poly (ester-amides), poly(carbonates), poly(urethanes), poly(ester urethanes), and copolymers, polymer alloys, polymer mixtures, or other materials, combinations or mixtures of these and/or other materials.

Although wells 36 and 80 are indicated in the figures, it will be understood that in some embodiments, a Janatpour connector having features of the invention may not have such wells (i.e., such wells are optional). It will be understood that a baffle (e.g., 60) need not be included in the systems, methods, and kits of the invention (i.e., such baffles are optional). In addition, in some embodiments of Janatpour connectors having features of the invention, a Janatpour connector may have multiple baffles, or multiple wells, or may have multiple baffles and multiple wells. It will be understood that any hollow connecting device, whether tubular or of other shape, may be used in devices having features of the invention, so that, for example, element 18 of FIG. 1, or element 104 of FIG. 6, or other elements shown as tubes may be of any suitable shape.

It will be understood that all features and elements of the invention disclosed herein may be combined together with another one or more of the other features or elements of the invention, even though such elements may not have been shown or described together in a particular figure or embodiment, or may have been described or shown in conjunction with only a subset of other features or elements.

Also provided are kits including a Janatpour connector having features of the invention. In embodiments, a kit having features of the invention includes a Janatpour connector having features of the invention and instructions for the assembly and/or use of the Janatpour connector. In embodiments, a kit having features of the invention includes a Janatpour connector having features of the invention and cotton swabs or other cleaning aids suitable for cleaning the interior of a Janatpour connector. In embodiments where the Janatpour connector has a well with a removable portion, such as a removable well base (e.g., where the base of the well may be screwed on or off, or may removably snap into place), a kit may include one or more replacement well bases. It will be understood that a kit may include any combination of Janatpour connectors, instructions, cleaning aids, replacement bases, and may further include other elements as well. For example, a kit having features of the invention may include instructions for the use of a Janatpour connector, and/or for the cleaning of a Janatpour connector, and may include other instructions.

A method for using a Janatpour connector having features of the invention includes a method for providing respiratory therapy exercise for a patient, in which the patient, healthcare provider, family member, or other person (a) connects a Janatpour connector 12 or 58 having a control port to a tracheostomy tube connected to the patient's trachea; (b) connecting the Janatpour connector 12 or 58 to a respiratory therapy exercise device, effective to operably connect said tracheostomy tube and said trachea to a respiratory therapy exercise device; and (c) occluding said control port, effective to provide said patient with respiratory therapy exercise upon respiration. The occlusion of the control port may be by, for example, a finger or a portion of a finger applied to the control port, effective to occlude (at least partially) airflow via the control panel. Such a finger may be, for example, the finger of a patient. Alternatively, or in addition, a lid may cover (at least partially) a control port, e.g., by action of a finger. A respiratory therapy exercise device comprising a tube having a bore within a tube wall, said tube being configured to connect with a tracheostomy tube and having therein a control port configured to provide a shunt airway path when open, and configured to leave substantially only a single airway path when the control panel is closed, said single airway path being via said bore.

All patents, patent applications, and publications disclosed herein are hereby incorporated by reference.

The invention claimed is:

1. A tracheostomy tube connector (Janatpour connector) having an open proximal end and an open distal end, comprising a wall defining a bore connecting said proximal end with said distal end, said proximal end being configured to engage a tracheostomy tube, said distal end being configured to engage a respiratory therapy exercise device or a tube operably connected with a respiratory therapy exercise device, said wall further comprising a control port, said control port comprising a control port opening, said control port opening providing an opening through said wall disposed between said proximal end and said distal end and operably connected with said bore, and further comprising a well disposed within said bore and operably connected with said bore.

2. A tracheostomy tube connector (Janatpour connector) having an open proximal end and an open distal end, comprising a wall defining a bore connecting said proximal end with said distal end, said proximal end being configured to engage a tracheostomy tube, said distal end being configured to engage a respiratory therapy exercise device or a tube operably connected with a respiratory therapy exercise device, said wall further comprising a control port, said control port comprising a control port opening, said control port opening providing an opening through said wall disposed between said proximal end and said distal end and operably connected with said bore, and further comprising a baffle within said bore and a well disposed within said bore and operably connected with said bore.

3. The Janatpour connector of claim 1, wherein said control port opening comprises a lip extending outwardly from said wall away from said bore, said lip defining at least a portion of said control port opening.

4. The Janatpour connector of claim 2, wherein said control port opening comprises a lip extending outwardly from said wall away from said bore, said lip defining at least a portion of said control port opening.

5. The Janatpour connector of claim 2, wherein said well is configured to receive fluid or debris from said baffle.

6. The Janatpour connector of claim 4, wherein said well is configured to receive fluid or debris from said baffle.

7. A system comprising a respiratory therapy exercise device and a Janatpour connector of claim 1 operably connected and configured effective to provide an airflow pathway between said Janatpour connector and said respiratory therapy exercise device.

8. A system comprising a respiratory therapy exercise device and a Janatpour connector of claim 2 operably connected and configured effective to provide an airflow pathway between said Janatpour connector and said respiratory therapy exercise device.

9. A kit including a Janatpour connector of claim 1, a respiratory therapy exercise device and instructions for their use.

10. A kit including a Janatpour connector of claim 2, a respiratory therapy exercise device and instructions for their use.

11. A respiratory therapy exercise method for a patient having a trachea, a tracheostomy and/or a tracheostomy tube connected to said trachea, said patient being in need of respiratory exercise with a respiratory exercise device, comprising: (a) connecting a Janatpour connector of claim 1 having a control port to a tracheostomy tube connected to said trachea of said patient; (b) connecting said Janatpour connector to a respiratory therapy exercise device, effective to operably connect said tracheostomy tube and said trachea to a respiratory therapy exercise device; and (c) at least partially occluding said control port, effective to provide said patient with respiratory therapy exercise during respiration.

12. The respiratory therapy exercise method of claim 11, wherein said at least partially occluding comprises occluding said control port with a finger.

13. A respiratory therapy exercise method for a patient having a trachea, a tracheostomy and/or a tracheostomy tube connected to said trachea, said patient being in need of respiratory exercise with a respiratory exercise device, comprising: (a) connecting a Janatpour connector of claim 2 having a control port to a tracheostomy tube connected to said trachea of said patient; (b) connecting said Janatpour connector to a respiratory therapy exercise device, effective to operably connect said tracheostomy tube and said trachea to a respiratory therapy exercise device; and (c) at least partially occluding said control port, effective to provide said patient with respiratory therapy exercise during respiration.

14. The respiratory therapy exercise method of claim 13, wherein said at least partially occluding comprises occluding said control port with a finger.

\* \* \* \* \*